US008590382B2

(12) United States Patent
Zaleski, Jr. et al.

(10) Patent No.: US 8,590,382 B2
(45) Date of Patent: Nov. 26, 2013

(54) METHOD FOR EVALUATING SHAPED CHARGE PERFORATION TEST CORES USING COMPUTER TOMOGRAPHIC IMAGES THEREOF

(75) Inventors: Theodore E. Zaleski, Jr., Spring, TX (US); Avrami S. Grader, Houston, TX (US); Henrique Tono, Houston, TX (US)

(73) Assignee: Ingrain, Inc., Houston, TX (US)

( * ) Notice: Subject to any disclaimer, the term of this patent is extended or adjusted under 35 U.S.C. 154(b) by 497 days.

(21) Appl. No.: 12/838,746

(22) Filed: Jul. 19, 2010

(65) Prior Publication Data

US 2011/0017447 A1 Jan. 27, 2011

Related U.S. Application Data

(60) Provisional application No. 61/227,651, filed on Jul. 22, 2009.

(51) Int. Cl.
*E21B 47/00* (2012.01)

(52) U.S. Cl.
USPC .................... 73/606; 166/250.01; 166/250.02

(58) Field of Classification Search
USPC ........................................................ 73/606
See application file for complete search history.

(56) References Cited

U.S. PATENT DOCUMENTS

| | | | |
|---|---|---|---|
| 6,220,371 B1 * | 4/2001 | Sharma et al. ................. | 175/50 |
| 2007/0255500 A1 * | 11/2007 | Pita et al. ........................ | 702/11 |

FOREIGN PATENT DOCUMENTS

RU 2213852 C2 10/2003

OTHER PUBLICATIONS

Bugani, Simone, Camaiti Mara, Luciano Morselli, Elke Van De Casteele, and Koen Janssens, "Investigating morphological changes in treated vs. untreated stone building materials by x-ray micro-CT," Analytical and Bioanalytical Chemistry, vol. 391, No. 4, Mar. 15, 2008, pp. 1343-1350.

Jones, Keith W., Huan Feng, Stanmire Tomov, William J. Winters, Masa Prodanovic, and Devinder Mahajan, "Characterization of methane hydrate host sediments using synchrotron-computed microtomography (CMT)," Journal of Petroleum Science and Engineering, vol. 56, No. 1-3, Mar. 31, 2007, pp. 136-145.

Notification of transmittal of the international search report and the written opinion of the international searching authority, International patent application No. PCT/US2010/042803, Dec. 28, 2010.

* cited by examiner

*Primary Examiner* — Hezron E Williams
*Assistant Examiner* — Gregory J Redmann
(74) *Attorney, Agent, or Firm* — Kilyk & Bowersox, P.L.L.C.

(57) ABSTRACT

A method for determining effects of perforation on a rock formation includes obtaining a sample of the rock formation. A perforation tunnel is created in the sample of the rock formation. The core sample is either subdivided into subsamples and a three dimensional tomographic image is made of each subsample and/or a three dimensional tomographic image is made of the sample of rock formation and the image thereof is segmented into sub images of selected subvolumes of the rock formation sample. At least one physical property of the rock formation is estimated from each tomographic image.

20 Claims, 3 Drawing Sheets

METHOD FOR EVALUATING SHAPED CHARGE PERFORATION TEST CORES USING COMPUTER TOMOGRAPHIC IMAGES THEREOF

CROSS-REFERENCE TO RELATED APPLICATIONS

Priority is claimed from U.S. Provisional Application No. 61/227,651 filed on Jul. 22, 2009.

STATEMENT REGARDING FEDERALLY SPONSORED RESEARCH OR DEVELOPMENT

Not applicable.

BACKGROUND OF THE INVENTION

1. Field of the Invention

The invention relates generally to the field of estimating material properties of porous media. More specifically, the invention relates to methods for estimating such properties using computer tomographic (CT) images of porous media such as subsurface rock formation.

2. Background Art

Estimating materials properties such as effective elastic moduli, electrical resistivity and fluid transport properties of porous media, an example of the latter being mobility of hydrocarbon in subsurface rock formations, has substantial economic significance. Methods known in the art for identifying the existence of subsurface hydrocarbon reservoirs, including seismic surveying and well log analysis, need to be supplemented with reliable methods for estimating how fluids disposed in the pore spaces of the reservoir rock formations will flow over time in order to characterize the economic value of such reservoir rock formations.

One method known in the art for estimating fluid transport properties is described in U.S. Pat. No. 6,516,080 issued to Nur. The method described in the Nur patent includes preparing a "thin section" from a specimen of rock formation. The preparation typically includes filling the pore spaces with a dyed epoxy resin. A color micrograph of the section is digitized and converted to an n-ary index image, for example a binary index image. Statistical functions are derived from the two-dimensional image and such functions are used to generate three-dimensional representations of the rock formation. Boundaries can be unconditional or conditioned to the two-dimensional n-ary index image. Desired physical property values are estimated by performing numerical simulations on the three-dimensional representations. For example, permeability is estimated by using a Lattice-Boltzmann flow simulation. Typically, multiple, equiprobable three-dimensional representations are generated for each n-ary index image, and the multiple estimated physical property values are averaged to provide a result.

It is also known in the art to use x-ray computer tomographic (CT) images of samples of rock for analysis. CT images are input to a computer program that segments the images into rock grains and pore spaces. The segmented image can be used as input to programs such as the Lattice-Boltzmann program described above to estimate formation fluid transport properties.

Wellbores drilled through subsurface formations typically have a pipe or casing cemented in place after drilling the wellbore is completed. The casing hydraulically isolates and protects the various rock formations and provides mechanical integrity to the wellbore. The wellbore is hydraulically connected to a formation from which fluid is to be withdrawn or injected by a process known as "perforating." Perforating is typically performed by inserting an assembly of explosive shaped charges into the wellbore and detonating the charges. See, for example, U.S. Pat. No. 5,460,095 issued to Slagle et al. The process of shaped charge perforating creates a tunnel or flow conduit that allows reservoir fluids to enter the wellbore and subsequently flow or be pumped out of the wellbore. However, by creating the perforation tunnels the physical parameters of the rocks surrounding the tunnel are often altered in such a manner as to restrict or reduce flow.

It is known in the art to test the effectiveness and performance of shaped charges. Testing is typically performed by the shaped charge manufacturer using a procedure specified by the American Petroleum Institute, Washington, D.C. ("API") known as Recommended Practice 43 ("RP43"). In performing RP43, a target material, typically in the shape of a cylinder, is placed proximate the shaped charge undergoing testing. A steel casing segment or plate and a layer of typical casing cement may be disposed between the target material and the shaped charge. The target material is typically a rock formation known as the Berea sandstone. After detonation of the shaped charge, the dimensions of the perforation made in the target are measured, and the fluid transport properties of the target may be measured in a laboratory. Laboratory evaluation of fluid transport properties can be difficult and expensive. Laboratory evaluation of perforated cores can also be highly inaccurate due to the presence of unknown fractures or heterogeneities within the core.

It is desirable to be able to estimate or determine fluid transport properties of perforation test targets without the need for full laboratory evaluation.

SUMMARY OF THE INVENTION

A method according to one aspect of the invention for determining effects of perforation on a rock formation includes obtaining a sample of the rock formation. A perforation tunnel is created in the sample of the rock formation. The core sample is either subdivided into subsamples and a three dimensional tomographic image is made of each subsample and/or a three dimensional tomographic image is made of the sample of rock formation and the image thereof is segmented into sub images of selected subvolumes of the rock formation sample. At least one physical property of the rock formation is estimated from each tomographic image.

Other aspects and advantages of the invention will be apparent from the following description and the appended claims.

DETAILED DESCRIPTION

Figure 1A:
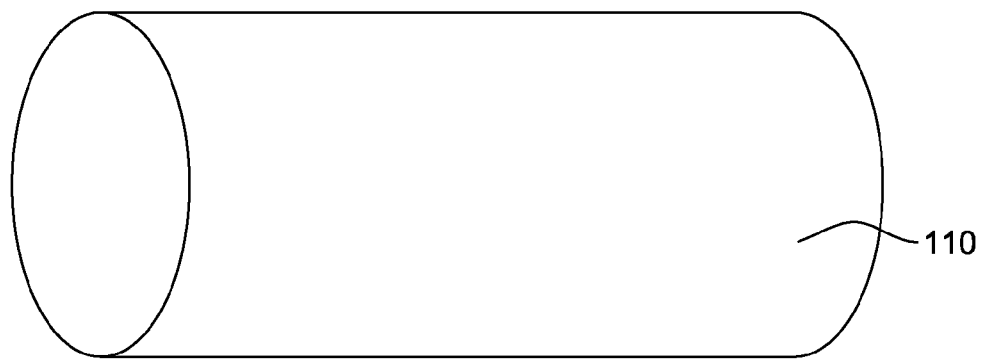
FIG. 1A shows a side view of an example Berea sandstone perforating test target core.
Figure 1B:
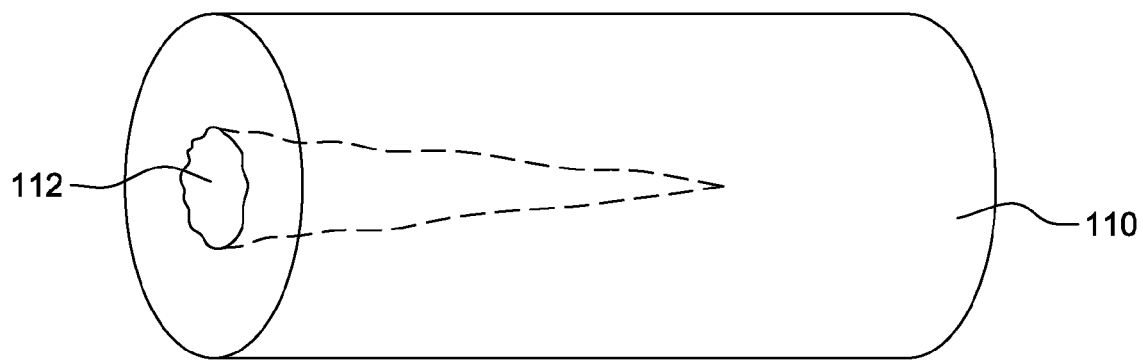
FIG. 1B shows the core of FIG. 1A after a shaped charge is detonated therethrough.
Figure 1C:
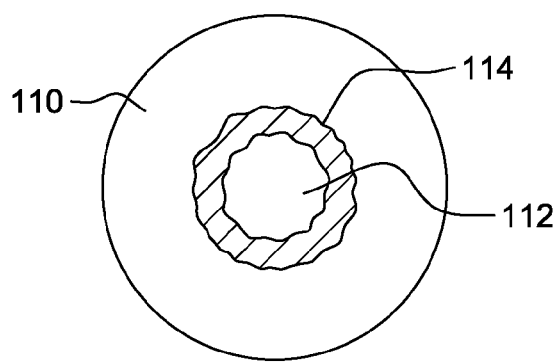
FIG. 1C shows an end view of the core of FIG. 1B to illustrate altered rock formation in an annular volume surrounding the perforation tunnel.

FIG. 1A shows a side view of an example test core 110 made of a rock formation known as Berea sandstone as discussed in the Background section herein. The test core 110 may be prepared according to the test procedure API RP43 referred to in the Background section herein. While test procedure API RP43 specifies Berea sandstone, the present invention is equally applicable to testing of other rock formations. FIG. 1B shows the test core 110 after detonation of a shaped charge in a test performed, for example, according to RP43. A perforation tunnel 112 is created by the action of the shaped charge upon detonation. Operation of shaped charges and how they create perforation tunnels is explained, in a non-limiting example, in U.S. Pat. No. 5,567,906 issued to Reese et al. An end view of the core sample 110 is shown in FIG. 1C to illustrate a zone 114 that occupies a roughly annular volume surrounding the perforation tunnel 112 in which the structure of the rock formation is altered to some extent by the action of the "jet" created by the shaped charge detonation. Such alteration within the zone 114 may also affect the fluid transport properties of the rock formation.

Figure 1D:
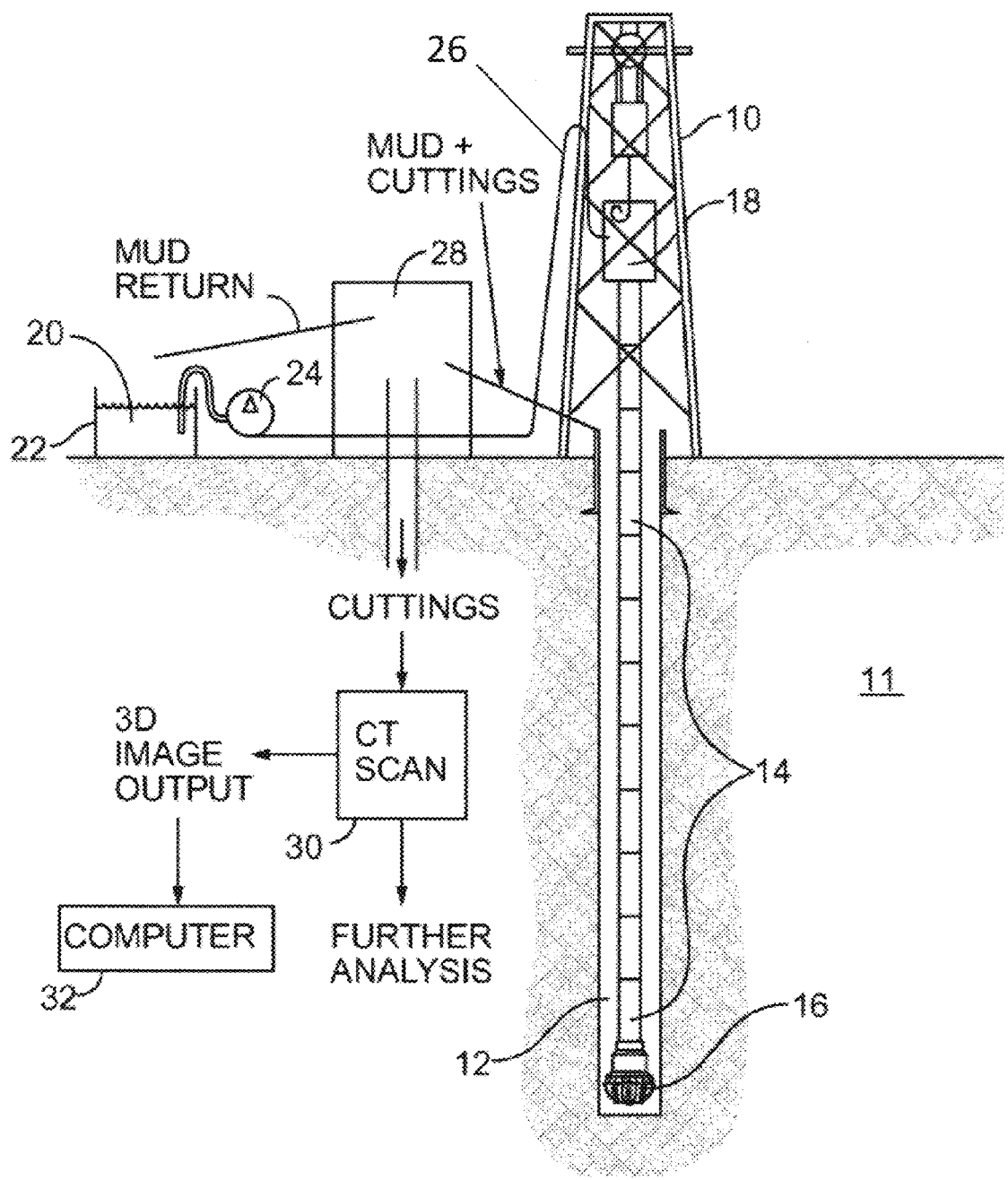
FIG. 1D shows an example of well drilling to obtain core samples.

An example of drilling a wellbore to obtain samples of rock formations for evaluation by examples of a method according to the invention will be explained with reference to FIG. 1D. A drilling unit or "rig" 10 is disposed at the Earth's surface. The rig 10 includes lifting equipment (not shown separately) for raising and lowering one of several types of device used to rotate a drill string 14. The device, shown at 18 in the present example may be a top drive, although the use of a top drive is not a limit on the scope of the invention. The drill string 14 is assembled by threadedly coupling segments of drill pipe end to end. A drill bit 16 is disposed at the lower end of the drill string 14 and cuts through subsurface rock formations 11 to form a wellbore 12. During the drilling of the wellbore 12, the rig 10 is operated to cause some of the axial load (weight) of the drill string 14 to be applied to the drill bit 16. The top drive 18 rotates the drill string 14 and the drill bit 16 at the lower end thereof. The combination of axial load and rotation causes the drill bit 16 to cut through the formations 11.

The rig 10 includes a tank or pit 22 having drilling fluid ("mud") 20 stored therein. A pump 24 lifts the mud 20 and discharges it through suitable flow lines 26 so that the mud 20 passes through an internal passage in the drill string 14, whereupon it is discharged through suitable orifices or courses in the drill bit 16. The discharged mud 20 cools and lubricates the drill bit 16 and lifts the cuttings generated by the bit 16 to the Earth's surface. The cuttings and mud thus lifted enter separation and cleaning devices, shown generally at 28 and including, for example, devices known as "degassers" and "shale shakers" to remove the cuttings and contamination from the mud 20. The mud after such cleaning is returned to the pit 22 for subsequent use in drilling the wellbore 12.

When the wellbore reaches a depth proximate a particular formation of interest, the drill bit 16 may be replaced by a core drilling bit (not shown) that may recover a substantially cylindrical core sample of the rock formation of interest. The core sample (110 in FIG. 1A) may be prepared into one or more perforation test cores shaped as explained with reference to FIGS. 1A, 1B and 1C, and perforated according to the conditions specified in RP43. It will be appreciated by those skilled in the art that to use a drilled core sample of the rock formation, it is desirable for the diameter of the core sample to be sufficient to enable perforation testing to be performed in a direction transverse to the axis of the core sample. This is because a drilled core sample is obtained by drilling along the axis of the wellbore, while typical wellbore perforations are made in a direction transverse to the axis of the wellbore. Thus, to simulate how the particular formation will actually be affected by perforation, the directionality of the rock sample with respect to the perforation direction can be important.

In other examples, samples of rock may be obtained from surface outcrops of the formation or near surface deposits of the rock formation. Such samples may be perforation tested in a direction that is expected to be similar to the direction of perforations in a wellbore drilled and cased through such formation. At present, using samples obtained from surface outcrops of rock formations is preferred. It is also known in the art to drill samples of the formation through the wellbore wall transverse to the wellbore axis using a specialized drilling instrument.

Figure 1E:
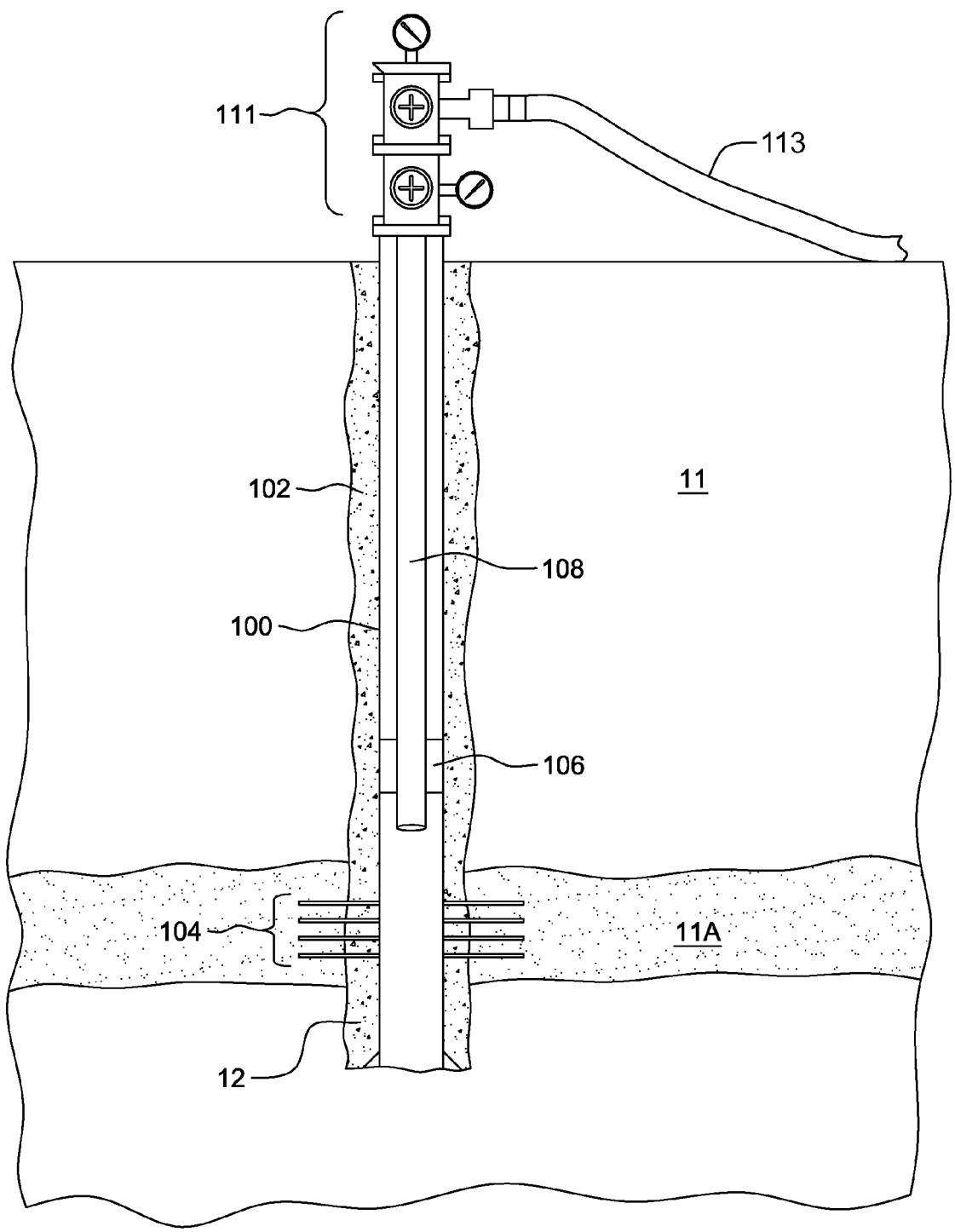
FIG. 1E shows an example of a completed wellbore with cemented in place casing having perforations therein in a reservoir formation.

FIG. 1E shows the wellbore after the drilling operations explained with reference to FIG. 1D have been completed. At the end of the drilling procedure, a steel pipe or casing 100 may be inserted into the wellbore 12. Cement 102 is then typically pumped through the interior of the casing 100, whereupon it travels through the bottom end thereof, and into the annular space between the wall of the wellbore 12 and the exterior of the casing 100. After the cement 102 has sufficiently cured, the remaining components of the wellbore 12 may be installed. In one procedure, an annular sealing element 106 called a packer is inserted into the casing 100 to a selected depth, typically above a depth of a reservoir formation 11A in the subsurface formations 11. A tubing 108 may be sealingly engaged with the packer 106, and wellhead equipment 111 may be installed at the top of the casing 100 and tubing 108. The wellhead equipment 111 may include control valves and may ultimately be coupled to a discharge conduit 113. Perforations 104 may be made through the casing 100, cement 102 and into the reservoir formation 11A. The perforations 104 may be made prior to inserting the packer and tubing using, for example, a casing perforating gun assembly (not shown). The perforations 104 may alternatively be made with a "tubing conveyed" perforating gun assembly (not shown) that is installed simultaneously with the tubing 108, and actuated, for example by applying fluid pressure to the tubing 108 or dropping an actuation tool (not shown) into the tubing 108. Alternatively, the perforations 104 may be made after insertion of the packer and tubing using a "through tubing" perforating gun assembly. Other methods for creating the perforations 104 are known in the art. The method of the present invention is intended to determine how the creation of the perforations 104 changes one or more petrophysical properties of the reservoir formation 11A, in particular the fluid transport properties.

In the present example, a perforated test core sample (e.g., 110 in FIG. 1A) may have taken therefrom small samples of the formation beginning laterally near the perforation tunnel (112 in FIG. 1) and continuing successively laterally outwardly. One or more samples may be taken near the lateral edge of the core sample near the back end thereof, where the perforation tunnel may not have caused material effect on the fluid transport properties of the rock formation. Alternatively, samples may be taken from unperforated core (e.g., as 110 in FIG. 1A). If samples from an unperforated test core are used, a perforation may be created in the test core, and subsequent samples may be taken from the perforated test core for comparative analysis.

The samples may be transported to a computer tomographic ("CT") scanner 30, which may use x-rays for analysis of internal structure of the cuttings, for generation of three dimensional (3D) images of the test core sample (110 in FIG. 1A). The images so generated may be in numerical form and their content will be further explained below. After CT scanning, the test cores may be saved for further analysis or may be suitably discarded.

In a practical implementation of core analysis according to the invention, the state of the rock formation prior to perforating can be determined by extracting relatively small portions of the core sample after the test perforating is performed. The state of the rock formation after perforation can be characterized by CT scanning the small samples and estimating fluid transport properties of the foregoing small samples as explained below.

In an alternative example, a CT image of the entire core may be made using suitable CT imaging devices. The CT image may be made prior to creating the perforation tunnel, and thereafter, or the CT image may be made only after creating the perforation tunnel. The CT image(s) may be segmented into sub images of the entire volume of the core sample similar in volume and position to the physical small samples taken from the entire core sample as explained above.

The extent to which the rock has been affected by perforating by examination (i.e., CT scan and analysis of the CT scan images thereof) of the small volume samples of the core obtained at progressively greater radial distances from the perforation tunnel axis until the determined fluid transport properties are substantially equal to those of the unaltered rock formation. It is thus possible to quantify the lateral extent of and the magnitude of the formation alteration caused by perforating and to map its radial distribution with respect to the perforation tunnel axis CT scan imaging of the test core small samples can be used in the invention to produce a numerical object that represents the material sample digitally in the computer 32 for subsequent numerical simulations of various physical processes, such as viscous fluid flow (for permeability estimation); stress loading (for the effective elastic moduli); electrical current flow (for resistivity); and pore size distribution for nuclear magnetic resonance relaxation time properties, including distribution of relaxation time.

The CT scan images produced by the CT scanner may be stored or displayed in a computer and can be used as input to one or more rock property characterization models. In the present example, the Lattice-Boltzmann method can be used to numerically solve Navier-Stokes equations for flow simulation. Such solution may be used to calculate permeability of simulated 3D volumes. The Lattice-Boltzmann method is a robust tool for flow simulation, particularly in media with complex pore geometry. See, for example. Ladd, *Numerical Simulations of Particulate Suspensions via a discretized Boltzmann Equation, Part* 1: *Theoretical Foundation*, J. Fluid Mech., v 271, 1994, pp. 285-309; Gunstensen et al., "*Lattice Boltzmann Model of Immiscible Fluids*, Phys. Rev. A., v. 43, no. 8, Apr. 15, 1991, pp. 4320-4327; Olsen et al., *Two fluid Flow in Sedimentary Rock Simulation, Transport and Complexity*, J. Fluid Mechanics, Vol. 341, 1997, pp. 343-370; and Gustensen et al., *Lattice-Boltzmann Studies of Immiscible Two-Phase Flow Through Porous Media,*" J. *of Geophysical Research*, V. 98, No. B4, Apr. 10, 1993, pp. 6431-6441).

The Lattice-Boltzmann method simulates fluid motion as collisions of imaginary particles, which are much larger than actual fluid molecules, but wherein such particles show almost the same behavior at a macroscopic scale. The algorithm used in the Lattice-Boltzmann method repeats collisions of these imaginary particles until steady state is reached, and provides a distribution of local mass flux. In accordance with the present invention, the Lattice-Boltzmann method is applied successfully for many pore structures, including cylindrical tubes, random densely packed spheres, and 3D rock samples digitized by CT scanning as explained above. See, for example, U.S. Pat. No. 6,516,080 issued to Nur.

It is also possible to estimate capillary pressure related flow characteristics from the pore structure determined using the 3D images processed as explained above. See, for example, U.S. Pat. No. 7,277,795 issued to Boitnott. Other properties of the rock formation that may be modeled include, without limitation, electrical formation resistivity factor, and compressional-wave and shear-wave acoustic velocity. Any or all of the foregoing estimated physical properties may be stored and/or displayed in the computer (32 in FIG. 1).

In a particular application of the foregoing technique for analyzing perforation test core samples, the fluid transport properties determined above on perforated core samples (e.g., FIG. 1B) of a formation of interest can be input into conventional reservoir simulator computer programs to derive an estimate of expected fluid production from the wellbore. In a particular application of the foregoing technique, the foregoing image and fluid transport property determination may be made on an unaltered test core sample (FIG. 1A), and/or as explained above on a portion of the perforated test core obtained sufficiently distant from the perforation tunnel so as to have essentially unaltered petrophysical properties. A shaped charge may then be detonated to create a perforation tunnel (FIG. 1B). The imaging and fluid transport property determination may then be repeated on small samples of the perforated test core at successively larger radial distances from the perforation tunnel axis as explained above.

Once a reservoir model is developed using the segmented images of the perforated test core, a number of other applications that use the images become possible, such as predicting changes in rock formation flow capacity resulting from changes in relative permeability. Relative permeability may change due to water invasion or gas coning, chemical or other stimulation, re-perforating the casing in a selected formation or blockage of existing perforations in the wellbore Methods according to the invention also can enable shaped charge manufacturers to determine how changes in shaped charge explosive type and weight, geometry, and materials affect the flow properties of various rock formations in addition to those commonly used for testing and QC purposes. The topology of the perforation tunnel can be mapped in detail using the segmented images The thickness of the damaged zone (14 in FIG. 1C) can be measured and quantified in terms of grain sizes and distribution compared to the unaffected portion of the core sample. Location of metal debris from the shaped charge jet in the perforation tunnel (112 in FIG. 1B) is also facilitated.

End users (operators) can develop specialized techniques for the use of perforating systems during well completion or repair. The amount of pressure differential (underbalance or overbalance), standoff, shot density (numbers of shaped charges used per unit axial length of wellbore casing), and selection of shaped charge type can also be evaluated. Such evaluated may enable optimization of perforating system cost by potentially reducing the number of perforations required and the total amount of explosive used. It may also be possible to optimize perforation techniques in a particular wellbore to compensate for the relative attitude of the formation (the direction of the bedding planes with respect to the wellbore axis).

While the example implementation herein is described in terms of jet perforating using explosive shaped charges, it should be clearly understood that the process described herein also applies to other methods of creating hydraulic openings in a well casing into a rock formation, including, without limitation, bullet perforating, hydraulic jetting, laser perforating, rotary boring, etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining effects of perforation on a rock formation, comprising:
    obtaining a sample of the rock formation;
    creating a perforation tunnel in the sample of the rock formation;
    at least one of subdividing the core sample into subsamples and making a three dimensional tomographic image of each subsample by utilizing x-ray computer tomographic imaging and making a three dimensional tomographic image of the sample of the rock formation and splitting the image thereof into sub images of selected subvolumes of the rock formation sample; and estimating at least one physical property of the rock formation from each tomographic image; and
    utilizing values of the said at least one physical property of each subsample along with subsample's distance from the tunnel axis as a function describing radial profiles of the effect of perforation on the rock formation.

2. The method of claim 1 wherein the at least one physical property comprises permeability.

3. The method of claim 2 wherein permeability is estimated using the Lattice-Boltzmann approximation.

4. The method of claim 1 wherein the at least one physical property comprises electrical resistivity formation factor.

5. The method of claim 1 wherein the at least one physical property comprises acoustic compressional velocity.

6. The method of claim 1 wherein the at least one physical property comprises acoustic shear velocity.

7. The method of claim 1 wherein the sample of the rock formation comprises a drilled core.

8. The method of claim 1 wherein the sample of the rock formation comprises a surface outcrop sample.

9. The method of claim 1 further comprising determining a topology of the perforation tunnel.

10. The method of claim 1 wherein the perforation tunnel is created by detonating a shaped explosive charge.

11. The method of claim 1 wherein the making a perforation tunnel is performed before the making the three dimensional tomographic image, the method further comprising at least one of subdividing the core sample into subsamples and making a three dimensional tomographic image of each subsample and segmenting each image thereof and making a three dimensional tomographic image of the sample of the rock formation and segmenting the image thereof into sub images of selected subvolumes of the rock formation sample; and estimating at least one physical property of the rock formation from each tomographic image for the rock formation prior to making the perforation tunnel therein.

12. The method of claim 1 further comprising entering the radially profiled physical property as input to a new reservoir simulation and estimating fluid flow from a subsurface reservoir from the simulation.

13. A method for determining effects of perforation on a rock formation, comprising:
    obtaining a sample of the rock formation;
    creating a perforation tunnel in the sample of the rock formation;
    at least one of subdividing the core sample into subsamples and making a three dimensional tomographic image of each subsample by utilizing x-ray computer tomographic imaging and making a three dimensional tomographic image of the sample of the rock formation and segmenting the image thereof into sub images of selected subvolumes of the rock formation sample; and estimating at least one physical property of the rock formation from each tomographic image;
    obtaining samples at a plurality of radial distances from an axis of the perforation tunnel and repeating the making an image, segmenting the image and estimating at least one physical property to obtain a radial profile of the at least one physical property;
    entering the radially profiled physical property as input to a reservoir simulation and estimating fluid flow from a subsurface reservoir from the simulation.

14. The method of claim 13 wherein the at least one physical property comprises permeability.

15. The method of claim 14 wherein permeability is estimated using the Lattice-Boltzmann approximation.

16. The method of claim 13 wherein the at least one physical property comprises electrical resistivity formation factor, acoustic compressional velocity, or acoustic shear velocity, or any combinations thereof.

17. The method of claim 13 wherein the sample of the rock formation comprises a drilled core.

18. The method of claim 13 wherein the sample of the rock formation comprises a surface outcrop sample.

19. The method of claim 13 further comprising determining a topology of the perforation tunnel.

20. The method of claim 13 wherein the perforation tunnel is created by detonating a shaped explosive charge.

* * * * *